US008081732B2

(12) United States Patent
Bruder et al.

(10) Patent No.: US 8,081,732 B2
(45) Date of Patent: Dec. 20, 2011

(54) CORRECTING TRANSVERSE SCATTERING IN A MULTI-EMITTER CT SCANNER

(75) Inventors: Herbert Bruder, Höchstadt (DE); Rainer Raupach, Heroldsbach (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/753,960

(22) Filed: Apr. 5, 2010

(65) Prior Publication Data

US 2010/0189213 A1 Jul. 29, 2010

Related U.S. Application Data

(63) Continuation of application No. 12/289,566, filed on Oct. 30, 2008, now abandoned.

(30) Foreign Application Priority Data

Nov. 2, 2007 (DE) .......................... 10 2007 052 448

(51) Int. Cl.
*G01N 23/00* (2006.01)

(52) U.S. Cl. ................................. 378/7; 378/9

(58) Field of Classification Search .................. 378/4, 5, 378/9, 19, 90, 86, 88, 89, 91, 7
See application file for complete search history.

(56) References Cited

U.S. PATENT DOCUMENTS

| 5,479,021 | A | 12/1995 | Morgan et al. |
| 6,377,652 | B1 | 4/2002 | Perry |
| 2004/0079232 | A1 | 4/2004 | Groh et al. |
| 2004/0213371 | A1* | 10/2004 | Bruder et al. ..................... 378/9 |
| 2005/0089134 | A1 | 4/2005 | Bruder et al. |
| 2007/0086561 | A1 | 4/2007 | Bruder et al. |
| 2007/0253525 | A1 | 11/2007 | Popescu |
| 2008/0043912 | A1* | 2/2008 | Harding ......................... 378/71 |
| 2008/0226020 | A1 | 9/2008 | Proksa |

FOREIGN PATENT DOCUMENTS

| DE | 10232429 | 1/2004 |
| DE | 102005048397 | 4/2007 |
| EP | 0654684 | 5/1995 |
| WO | WO 2006034585 | 4/2006 |
| WO | WO 2007031898 | 3/2007 |

OTHER PUBLICATIONS

Elsen, Shor, Mardor: "CdTe and CdZnTe X-Ray and Gamma-Ray Detectors for Imaging Systems" in IEEE Transactions on Nuclear Science, vol. 51, No. 3; Magazine; 2004.

Baba et al.: "Recent development of radiation measurement instrument for industrial and medical applications," in Nuclear Instruments and Methods in Physics Reasearch A 458 (2001); Magazine: 2001.

* cited by examiner

*Primary Examiner* — Hoon Song

(74) *Attorney, Agent, or Firm* — Harness, Dickey & Pierce, P.L.C.

(57) ABSTRACT

A multi-emitter computed tomography scanner is disclosed, including a plurality of x-ray emitter/detector arrangement pairs arranged offset at an angle to one another. In at least one embodiment, the detector arrangements of the pairs are designed to be energy selective.

11 Claims, 2 Drawing Sheets

CORRECTING TRANSVERSE SCATTERING IN A MULTI-EMITTER CT SCANNER

PRIORITY STATEMENT

The present application is a continuation of U.S. application Ser. No. 12/289,566, filed on Oct. 30, 2008, now abandoned which claims priority under 35 U.S.C. §119 to German patent application number DE 10 2007 052 448.1, filed on Nov. 2, 2007. The entire contents of each of these applications are incorporated herein by reference.

FIELD

Embodiments of the present invention generally relate to multi-emitter computed tomography scanners. In at least one embodiment, such scanners include a plurality of x-ray emitter/detector pairs, the optical axes of which are offset at an angle to one another.

BACKGROUND

Even though more than two x-ray emitter/detector pairs can be provided in such a computed tomography scanner, the following background description is intended to be limited to systems which have two x-ray emitters. Such systems, which are also referred to as dual-source CT systems, were developed only a few years ago and have substantial advantages over systems with only one x-ray source. Using a dual-source computed tomography scanner (DSCT scanner), it is possible to take images at a significantly higher speed. It is even possible to obtain images of the highest quality and with the most accurate details of weakly or irregularly beating hearts, and at the same time lower the radiation dose.

As has been mentioned previously, two x-ray emitter/detector pairs are arranged with an angular offset of 90° in the case of a dual-source CT system. Here, there is a problem in that transversely scattered x-ray radiation is respectively incident on the crossed detector. There are a number of approaches for correction, some of which are based on modeling and others detect the signal of the transverse scattering in measurements and then correct these in a preprocessing step. This makes it possible to reduce as far as possible the signal of the transverse scattering. However, the quantum noise of the scattered signal remains in the data to be evaluated.

SUMMARY

In at least one embodiment of the present invention, a multi-emitter computed tomography scanner is disclosed, in which the contrast-to-noise ratio in the output signals is improved by extensive suppression of transverse scattered signals.

BRIEF DESCRIPTION OF THE DRAWINGS

In the following text, the invention will be explained in more detail based on the description of an example embodiment in conjunction with the appended drawings, in which.

DETAILED DESCRIPTION OF THE EXAMPLE EMBODIMENTS

Figure 1:
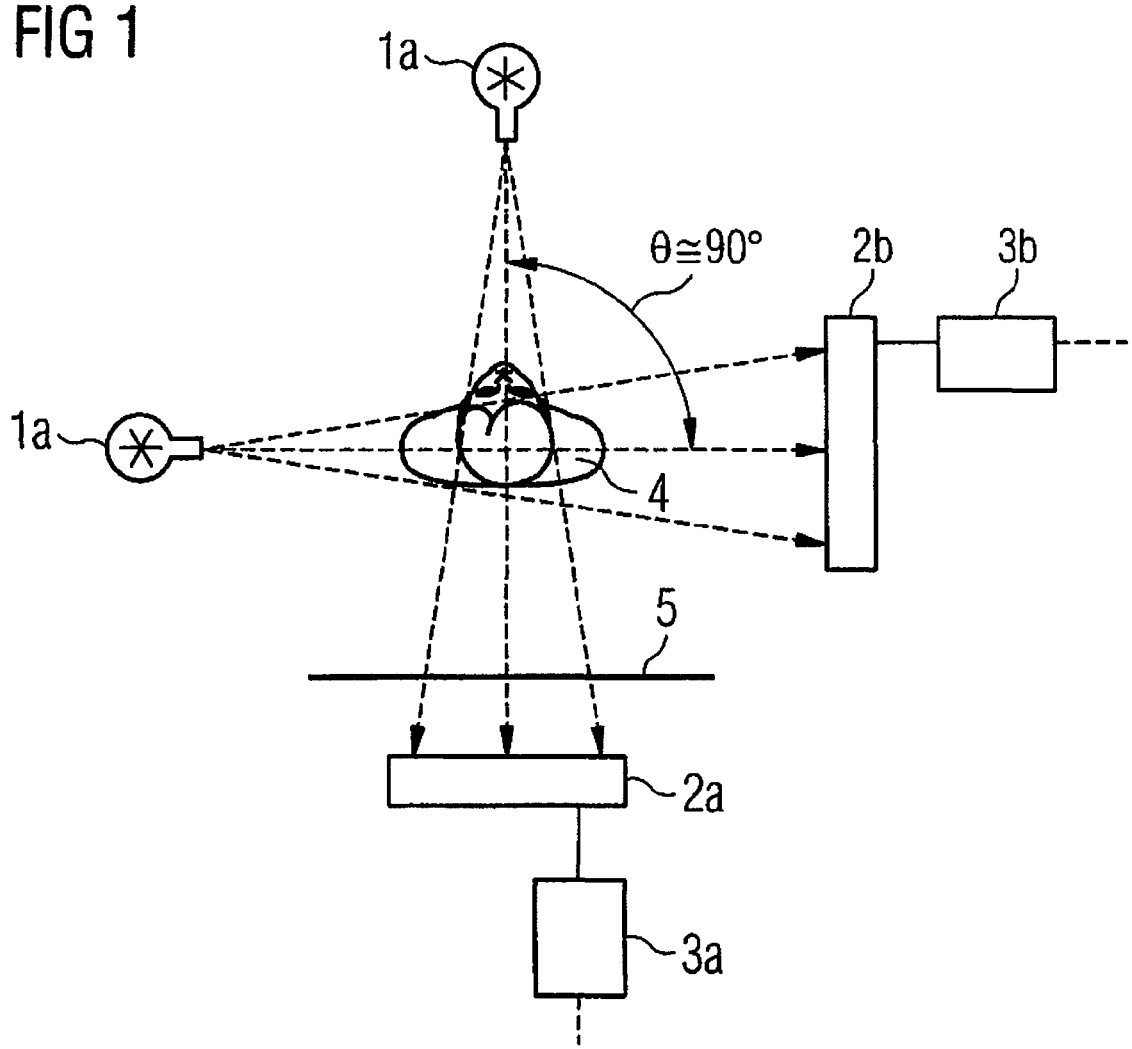
FIG. 1 shows a very much simplified design of part of a dual-source computed tomography scanner.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows the arrangement of two x-ray emitter/detector pairs 1a, 2a; 1b, 2b, which are arranged offset at an angle of 90° with respect to one another.

A measurement object 4, such as a patient, is arranged in the crossing region of the beam paths of the two x-ray emitters 1a, 1b. The output radiation of the x-ray emitter 1a passes through the measurement object 4 and is detected by the detector 2a, lying on the optical axis of the x-ray emitter 1a. The same holds for the x-ray emitter/detector pair 1b, 2b. The measurement signals of the two detectors 2a, 2b are conditioned in the downstream signal processing units 3a and 3b, as is explained in more detail below, and are processed further for imaging in evaluation electronics (neither described nor illustrated here).

The arrangement of a detector 2a, 3a proper, evaluation electronics 3a, 3b arranged downstream thereof and possibly a filter 5 arranged in the beam path between the x-ray beams and the detector will be referred to as a detector arrangement in the following text.

In addition to the beams respectively transmitted through the measurement object, there is also incident, by way of example, on the detector 2a x-ray radiation which is emitted by the x-ray emitter 1b and scattered at the measurement object 4 with a scattering angle θ of approximately 90°. This transverse scattered radiation proportion corrupts the measurement signal in the respectively crossed detector.

The energy of the transversely scattered wave can be calculated as follows:

Compton scattering present here results in the following Compton-shift:

$$\Delta\lambda = \lambda - \lambda' = \lambda_c \cdot (1 + \cos(\theta)),$$

where $\lambda_c$ is the Compton wavelength, θ=90° is the scattering angle, and λ and λ' are the wavelengths of the incident and scattered waves. Using the relationship $$\lambda = \frac{h \cdot c}{E},$$

where h is Planck's constant and c is the speed of light in a vacuum, the energy of the scattered wave can be calculated using $$E_{out} = \frac{E_{in}}{1 + \frac{\lambda_c}{h \cdot c} \cdot E_{in}}.$$

Figure 2:
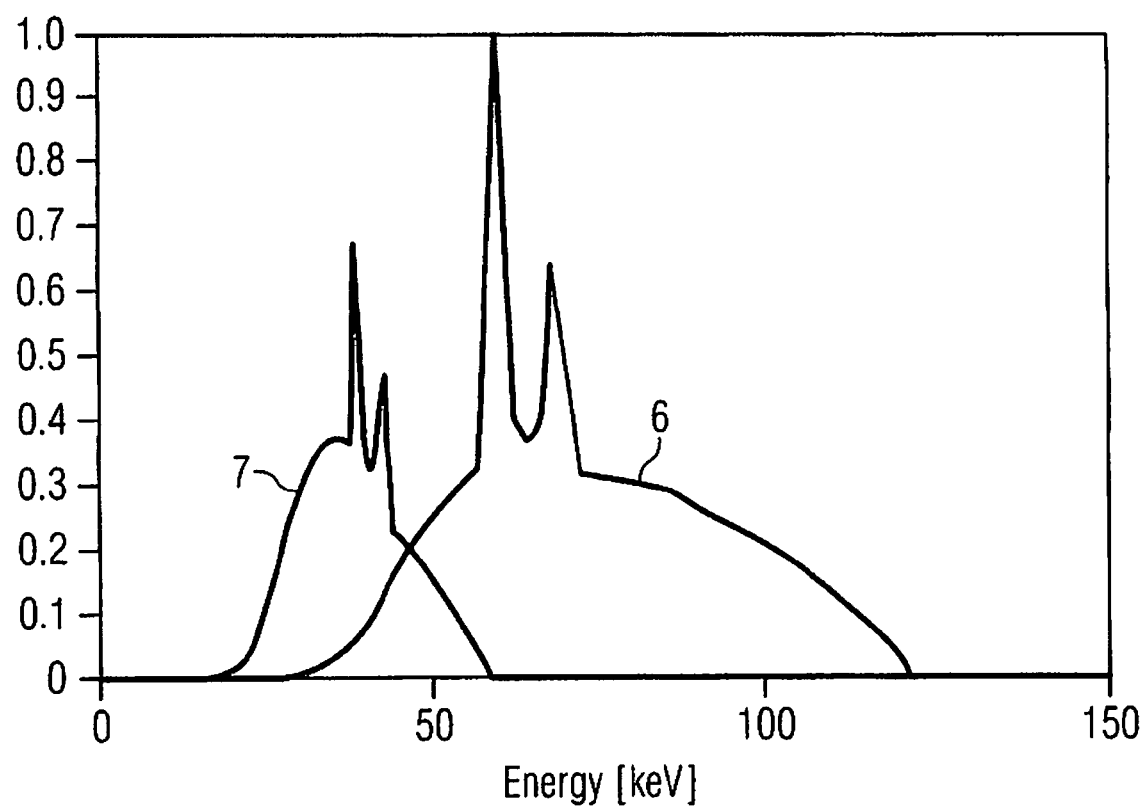
FIG. 2 shows a spectrum of transverse scattering compared to the spectrum of the primary radiation in a dual-emitter CT scanner.

FIG. 2 shows the spectrum 6 of the primary radiation which is transmitted through a 200 mm thick absorber for an example case, where the tube voltage of an x-ray emitter is 120 kV. Next to this on the left, toward lower energies, is the spectrum of the transverse scattering 7.

It can be seen that these two spectra 6, 7 hardly overlap. In the illustrated examples, this results, for a tube voltage of 120 keV and an invariant mass energy of $E_{in}$=70 keV, in a transversely scattered wave energy $E_{out}$ of approximately 0.61·$E_{in}$. Thus, it is possible to separate the respective primary signals and scattered signals into different energy bins. If, as shown in FIG. 1 there is now arranged only in the beam path of the emitter/detector pair 1a, 2a, a filter 5 which only transmits radiation with an energy which is significantly higher than the energy of the transversely scattered wave (in the example shown in FIG. 2, radiation with an energy of ≧50 key), then the scattered signal is eliminated as far as possible from the measurement signal.

By way of example, such a filter 5 can comprise a radiation-transmissive substrate with a tin coating, a tin foil or a tin plate. The quantum noise of the transverse scattered signal, which undergoes the same Compton shift, is naturally also eliminated along with the transverse scattered signal.

In place of an energy-selective filter arranged in the beam path, the transverse scattered signals with the associated quantum noise can be separated from the primary signals using the method described in the following.

Thus, according to an example embodiment of the invention, it is likewise possible to use a quanta-counting detector to suppress the transverse scattered radiation and its quantum noise. A quanta-counting detector suitable for computed tomography imaging has a cadmium telluride layer as a sensor face. In this case, it is a directly converting semiconductor, which directly converts incident x-ray radiation into an electron flow. This flow is linear with respect to the number of incident quanta and can be detected using appropriate measurement electronics in an energy-resolved manner, that is to say it can be subdivided into a number of energy bins.

Evaluation electronics downstream of the detector can separate a predetermined low-energy energy bin, which contains the energy spectrum of the transverse scattered radiation, from a higher-energy energy bin and disregard the former bin in the subsequent further processing. Consequently, both the transverse scattered signal and the associated quantum noise of the transverse scattered signal are likewise eliminated, and the signal-to-noise ratio of the signal to be processed by the evaluation electronics is improved overall.

Although the described example embodiments referred to a dual-emitter CT scanner, it is obvious that the present invention is not limited to this number of emitter/detector pairs; rather it extends to CT systems having more than two emitter/detector pairs.

Further, elements and/or features of different example embodiments may be combined with each other and/or substituted for each other within the scope of this disclosure and appended claims.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reducing a share of scatter radiation in detector data obtained with detectors arranged at an angle offset and opposite-arranged X-ray radiators of a multi-radiator computed tomography (CT) system, wherein the X-ray radiators are configured to transmit X-ray radiation with a first energy spectrum onto a measuring object, and the measuring object emits scatter radiation with a second energy spectrum, the method comprising:

determining the first energy spectrum of the X-ray radiation transmitted by an X-ray radiator;

computing the second energy spectrum of the scatter radiation emitted by the measuring object based on a Compton scattering;

energy-selective measuring of X-ray radiation impinging on the detectors;

separating the measured X-ray radiation into at least two energy bins;

allocating the measured x-ray radiation to transmitted or respectively scattered radiation according to the separated at least two energy bins; and exclusively using detector data assigned to the transmitted X-ray radiation for imaging; wherein quanta-counting semiconductor detectors are used for the energy-selective measuring of the transmitted X-ray radiation and the scatter radiation, wherein the quanta-counting semiconductor detectors are configured to convert the X-ray radiation to an electron flow that is linear to the number of incident quanta, separate and detect the measured X-ray radiation into the at least two energy bins.

2. The method according to claim 1, wherein the following formula is used to compute the second energy spectrum:

$$E_{out} = \frac{E_{in}}{1 + \frac{\lambda_c}{hc} E_{in}},$$

wherein:

$E_{in}$=an energy of the transmitted X-ray radiation, and
$E_{out}$=an energy of the scatter radiation.

3. The method according to claim 1, wherein the detector data assigned to the transmitted X-ray radiation further processed at evaluation circuits, which follow the detectors in the detector arrangements, do not account for detector signals assigned to low-energetic energy bins.

4. The method according to claim 3, wherein a filter is used in the beam path between the measuring object and the detector for the radiator/detector arrangements, and wherein the filter only allows radiation having an energy that is essentially higher than the energy of the scatter radiation to pass through.

5. The method according to claim 1, wherein a filter is used in the beam path between the measuring object and the detector for the radiator/detector arrangements, and wherein the filter only allows radiation having an energy that is essentially higher than the energy of the scatter radiation to pass through.

6. The method according to claim 5, wherein a substrate with a tin coating is used as the filter.

7. A method for reducing a share of scatter radiation in detector data obtained with detectors arranged at an angle offset and opposite-arranged X-ray radiators of a multi-radiator computed tomography (CT) system, wherein the X-ray radiators are configured to transmit X-ray radiation with a first energy spectrum onto a measuring object, and the measuring object emits scatter radiation with a second energy spectrum, the method comprising:

determining the first energy spectrum of the X-ray radiation transmitted by an X-ray radiator;

computing the second energy spectrum of the scatter radiation emitted by the measuring object based on a Compton scattering;

energy-selective measuring of X-ray radiation impinging on the detectors;

separating the measured X-ray radiation into at least two energy bins;

allocating the measured x-ray radiation to transmitted or respectively scattered radiation according to the separated at least two energy bins; and exclusively using detector data assigned to the transmitted X-ray radiation for imaging;

wherein the following formula is used to compute the second energy spectrum:

$$E_{out} = \frac{E_{in}}{1 + \frac{\lambda_c}{hc} E_{in}},$$

wherein:

$E_{in}$=an energy of the transmitted X-ray radiation, and
$E_{out}$=an energy of the scatter radiation.

8. The method according to claim 7, wherein the detector data assigned to the transmitted X-ray radiation further processed at evaluation circuits, which follow the detectors in the detector arrangements, do not account for detector signals assigned to low-energetic energy bins.

9. The method according to claim 8, wherein a filter is used in the beam path between the measuring object and the detector for the radiator/detector arrangements, and wherein the filter only allows radiation having an energy that is essentially higher than the energy of the scatter radiation to pass through.

10. The method according to claim 7, wherein a filter is used in the beam path between the measuring object and the detector for the radiator/detector arrangements, and wherein the filter only allows radiation having an energy that is essentially higher than the energy of the scatter radiation to pass through.

11. The method according to claim 10, wherein a substrate with a tin coating is used as the filter.

* * * * *